United States Patent [19]
Chauvin et al.

[11] Patent Number: 5,589,601
[45] Date of Patent: Dec. 31, 1996

[54] PROCESS FOR THE DIMERIZATION, CO-DIMERIZATION AND OLIGOMERIZATION OF OLEFINS

[75] Inventors: Yves Chauvin, Le Pecq; Hélène Olivier, Rueil Malmaison, both of France

[73] Assignee: Institut Francais du Petrole, France

[21] Appl. No.: 528,519

[22] Filed: Sep. 15, 1995

[30] Foreign Application Priority Data

Sep. 16, 1994 [FR] France .................................. 94 11153

[51] Int. Cl.$^6$ ................ C07C 2/02; C07C 2/04; C07C 2/24
[52] U.S. Cl. .................. 585/513; 585/510; 585/512; 585/520; 585/527; 585/530
[58] Field of Search .................. 585/510, 512, 585/513, 520, 527, 530

[56] References Cited

U.S. PATENT DOCUMENTS 3,897,512  7/1975  Brown et al. .
5,059,739  10/1991  Hendriksen .............................. 585/513

*Primary Examiner*—Anthony McFarlane
*Assistant Examiner*—E. D. Irzinski
*Attorney, Agent, or Firm*—Millen, White, Zelano, & Branigan, P.C.

[57] ABSTRACT

The invention concerns a process for dimerization, co-dimerization and oligomerization of olefins, in particular α-olefins, with a catalytic composition resulting from a mixing at least one tungsten oxyhalide, at least one aryl isocyanate of diisocyanate, and at least one alkylaluminum halide.

15 Claims, No Drawings

PROCESS FOR THE DIMERIZATION, CO-DIMERIZATION AND OLIGOMERIZATION OF OLEFINS

SUMMARY OF THE INVENTION

An object of the present invention is to provide a process for dimerization, co-dimerization and oligomerization of olefins with a tungsten based catalytic composition.

A very large number of processes for dimerization and co-dimerization of olefins are known. Some of these processes use catalysts resulting from the interaction of tungsten halides, anilines and alkylaluminium halides in a chlorobenzene solvent. Such processes have been described in U.S. Pat. Nos. 3,784,629, 3,784,630, 3,784,613, 3,813,453 and 3,903,193. More recently, U.S. Pat. No. 5,059,739 has described an improvement to prior art processes, consisting of eliminating the hydrochloric acid which forms during the reaction before addition of the alkylaluminium halide. Only tungsten hexachloride and pentabromide are used in the examples. All these processes suffer from the use of tungsten halides which are costly, and from the use of chlorobenzene as a solvent, which is then difficult to separate from the products of the olefin dimerization, and from the liberation of a hydrohalogen acid.

It has now been discovered, and this consititutes an object of the present invention, a process for dimerization, co-dimerization and oligomerization of olefins by contact with a catalytic composition which results from mixing at least one tungsten oxyhalide, at least one aryl isocyanate and/or diisocyanate, which may or may not be substituted, and at least one alkylaluminium halide.

Tungsten salts which are suitable for use in the process of the invention have general formula $WO_mX_{4-n}$ where X is chlorine or bromine, m=1 or 2 and n=0, 1 or 2. These salts can in particular be of the type $WOX_4$, $WOX_3$, or $WO_2X_2$. Preferred compounds are tungsten oxytetrachloride, tungsten dioxydichloride and tungsten oxytribromide.

Isocyanates (I) and diisocyanates (II) which are suitable for use in the process of the invention have the following general formulae:

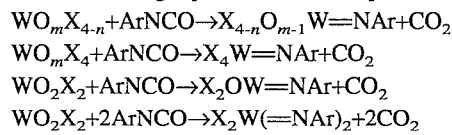

where $R^1$ to $R^5$ are hydrogen, halogens or hydrocarbon groups containing one to twelve carbon atoms. Preferred isocyanates are phenylisocyanate, 2,6-dimethylphenylisocyanate, 2,6-diisopropylphenylisocyanate, tolyldiisocyanate, 2,5-dimethylphenylisocyanane and 2,5-diisopropylphenylisocyanate.

Alkylaluminium halides which are suitable for use in the process of the invention have general formula $R_nAlX_{3-n}$ where R is a hydrocarbon radical containing two to six carbon atoms, X is chlorine or bromine and n is 1, 1.5 or 2. Examples of group R are ethyl, butyl, isobutyl or n-hexyl groups. Preferred alkylaluminium halides are dichloroethylaluminium, dichloroisobutylaluminium, ethylaluminium sesquichloride and chlorodiethylaluminium.

The composition can also contain a solvent, for example a hydrocarbon, halogenated hydrocarbon, or a dimerization, co-dimerization or oligomerization product.

The catalyst of the invention is preferably prepared in two stages. The composition of the invention thus results from mixing at least one alkylaluminium halide with the reaction product from mixing at least one tungsten oxyhalide with at least one aryl isocyanate and/or diisocyanate.

In the first step, the tungsten oxyhalide is reacted with the isocyanate or diisocyanate either pure or in the presence of a hydrocarbon, halogenated hydrocarbon or the dimerization reaction products, in an isocyanate/tungsten molar ratio of 1:1 to 2:1. During the reaction, one equivalent of carbon dioxide is released per isocyanate residue, in accordance with the following equations, for example:

$WO_mX_{4-n}+ArNCO \rightarrow X_{4-n}O_{m-1}W=NAr+CO_2$ $WO_mX_4+ArNCO \rightarrow X_4W=NAr+CO_2$ $WO_2X_2+ArNCO \rightarrow X_2OW=NAr+CO_2$ $WO_2X_2+2ArNCO \rightarrow X_2W(=NAr)_2+2CO_2$ This reaction can be carried out at a sufficient pressure (atmospheric pressure, for example) to allow the gas to be liberated in a suitable vessel and at a sufficient temperature for the liberation to be observed, advantageously at the boiling point of the hydrocarbon or halogenated hydrocarbon.

At this stage of the reaction, the imido complex can be isolated either in the form $X_4W=NAr$ or in the form of an addition product with an ether, for example $X_4W=NAr$, $Et_2O$, as described in "Inorganic Synthesis", 24, 194 (1986).

In a second step, the isolated complex, or at least a portion of the mixture from the first step, is reacted with the alkylaluminium halide in the presence or absence of a halogenated hydrocarbon or the dimerization, co-dimerization or oligomerization reaction products, in the presence or absence of the olefin whose reaction is to be catalyzed. The molar ratio between the aluminium compound and the tungsten compound is between 1 and 20, preferably between 2 and 15.

Preferred olefins for dimerization, co-dimerization or oligomerization using the catalytic composition of the invention and containing 2 to 10 carbon atoms are alpha olefins, in particular ethylene, propylene and but-1-ene.

The catalytic dimerization, co-dimerization or oligomerization reaction can be carried out in the presence of a solvent but it is preferably carried out in the absence of a solvent, in the products from the olefin reaction, either in a batch, part-open or continuous system. The reaction temperature is between 0° C. and 100° C., preferably between 30° C. and 80° C. The pressure is sufficient to maintain all or part of the reactant(s) in the liquid phase.

At the end of the reaction, the catalyst can be neutralized using any means known to the skilled person, in particular using anhydrous ammonia, then water or an aqueous acid.

EXAMPLES

The following examples illustrate the invention without limiting its scope.

EXAMPLE 1

Preparation of Catalyst 0.93 g of phenylisocyanate (7.85 mmoles) was added dropwise, with stirring, to a suspension of 2.68 g of tungsten oxytetrachloride (7.85 mmoles) in toluene (20 ml) and in an argon stream. The mixture was refluxed for 20 hours and

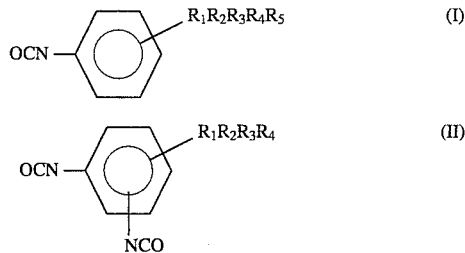

turned yellow-green. After returning to room temperature, vacuum evaporation of the toluene produced a dark green solid corresponding to the complex $Cl_4W=NPh$ (yield 73%).

Dimerization of Propylene 0.313 g (0.75 mmole) of this solid was suspended in 15 ml of toluene then injected into a stainless steel 150 ml autoclave provided with a double envelope and a magnetic stirrer, which had been dried under vacuum at 100° C. then kept under one atmosphere of propylene. The dichloroalkylaluminium (1.2 g; 9 mmoles) was injected into the reactor at room temperature, using a syringe, in a propylene atmosphere. The reactor was heated to 60 °C. and the liquid propylene, which had been stored and dried over a molecular sieve, was added to the reactor in fractions of 10 ml, depending on its consumption.

In Examples 1 to 6, after a given reaction time the autoclave was cooled no room temperature then the reaction was stopped by injection of anhydrous gaseous ammonia. The (liquid) reaction products were analyzed using gas phase chromatography on a PONA column.

The results are shown in Table 1.

EXAMPLE 2

The tungsten complex was prepared as described in Example 1. The green solid obtained was recrystallised from ether at −78° C. Dark green crystals of $Cl_4W=NPh, Et_2O$ were obtained which were used in catalysis in analogous manner to that described in Example 1. The results are shown in Table 1.

EXAMPLE 3

0.313 g (0.75 mmole) of the imido complex $Cl_4W=NPh$, prepared as described in Example 1, was suspended in 15 ml of toluene, in a Schlenk tube, then cooled to 0° C. 0.83 ml (1.1 g; 9 mmoles) of dichloroethylaluminium was added under a stream of argon. The green suspension turned red and dissolved in the toluene. This solution remained stable at room temperature in argon. It was injected at room temperature into the reactor, which had been held in a propylene atmosphere. The reactor was then heated to 60° C. and the liquid propylene was added as in Example 1. The results are shown in Table 1.

EXAMPLE 4

The catalyst was prepared as described in Example 3, using 2 equivalents of dichloroethylaluminium per equivalent of tungsten.

EXAMPLE 5

Preparation of Catalyst 2,6-dimethylphenylisocyanate (ArNCO) (1.1 ml; 7.9 mmoles) was added dropwise, with stirring, to a suspension of 2.49 g of tungsten oxytetrachloride (7.29 mmoles) in toluene (20 ml) in a stream of argon. The mixture was refluxed for 48 hours, turning yellow-brown. After returning to room temperature, vacuum evaporation of the toluene produced a brick red solid of the complex $Cl_4W=NAr$ (yield 73%).

Catalysis was effected as described in Example 1, but in chlorobenzene.

EXAMPLE 6

The complex was prepared (0.75 mole) as described in Example 5 then dissolved in 15 ml of chlorobenzene (red-brown). This solution underwent a catalysis test as described in Example 1. The results are shown in Table 1.

TABLE 1

| | Propylene introduced (ml) | Reaction time (hours) | Nature of imido group | Al/W (molar ratio) | Dimer selectivity (weight %) | Distribution of dimers (weight %/C$_6$) | | | | | | |
|---|---|---|---|---|---|---|---|---|---|---|---|---|
| | | | | | | M4P1 | DM2,3B1 | M4P2 | M2P1 | H | M2P2 | DM2,3B |
| Example 1 | 95 | 1 | phenyl | 12 | 90 | 0,82 | 60,9 | 3,4 | 30 | 0,2 | 1,9 | 0,4 |
| Example 2 | 95 | 1 | phenyl | 12 | 92,2 | 0,8 | 60,1 | 5,6 | 31,2 | 0,2 | 1,7 | 0,3 |
| Example 3 | 95 | 0,75 | phenyl | 12 | 92,4 | 0,6 | 60,2 | 5,4 | 31,5 | 1,9 | 0,3 | 0 |
| Example 4 | 95 | 1,1 | phenyl | 2 | 87 | 1 | 60,3 | 6 | 30,3 | 0,2 | 1,4 | 0,6 |
| Example 5 | 50 | 2.8 | 2,6-dimethyl phenyl | 12 | | | | | | | | |
| Example 6 | 95 | 4 | 2,6-dimethyl phenyl | 12 | 76,7 | 2,9 | 75.3 | 8,5 | 5,1 | 0,1 | 3,4 | 4,5 |

M4P1: 4-methyl pent-1-ene;
DM23B1: 2,3-dimethyl but-1-ene;
M4P2: 4-methyl pent-2-ene;
M2P1: 2-methyl pent-1-ene;
H: n-hexenes;
M2P2: 2 methyl pent-2-ene;
DM23B2: 2,3-dimethyl but-2-ene.

We claim:

1. A process for the dimerization, co-dimerizgation or oligomerization of olefins, comprising contacting said olefins under effective conditions with a catalytic composition which results from mixing at least one tungsten oxyhalide, at least one aryl isocyanate and/or diisocyanate, and at least one alkylaluminum halide.

2. A process according to claim 1, wherein the tungsten oxyhalide has general formula $WO_mX_{4-n}$ where X is chlorine or bromine, m=1 or 2 and n=0, 1 or 2.

3. A process according to claim 1, wherein the isocyanates (I) and diisocyanates (II) have the following general formulae:

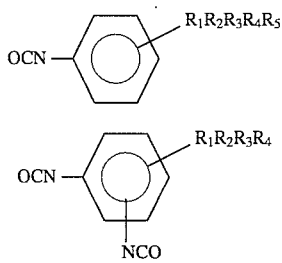

where $R_1$, $R_2$, $R_3$, $R_4$ and $R_5$ are selected from the group consisting of hydrogen, a halogen and a hydrocarbon group containing 1 to 12 carbon atoms.

4. A process according to claim 1, wherein the alkyluminum halide has general formula $R_n AlX_{3-n}$ where R is a hydrocarbon radical containing 2 to 6 carbon atoms, X is chlorine or bromine and n is 1, 1.5 or 2.

5. A process according to claim 1, wherein the tungsten oxyhalide is selected from the group consisting of tungsten oxytetrachloride, tungsten dioxychloride and tungsten oxytribromide.

6. A process according to claim 1, wherein the alkylaluminium halide is selected from the group consisting of dichloroethylaluminium, dichloroisobutylaluminium, chlorodiethylaluminium and ethylaluminium sesquichloride.

7. a process according to claim 1, wherein the alkylaluminum halide is selected from the group consisting of dichloroethylaluminum, dichloroisobutylaluminum, chlorodiethylaluminum and ethylaluminum sesquichloride.

8. A process according to claim 1, wherein the isocyanate/tungsten molar ratio is between 1:1 and 2:1.

9. A process according to claim 1, wherein the molar ratio between the aluminium and the tungsten compound is between 1 and 20.

10. A process according to claim 1, wherein the composition also comprises a solvent selected from the group consisting of hydrocarbons, halogenated hydrocarbons and the products of the dimerization, co-dimerization or oligomerization reaction.

11. A process according to claim 1, wherein the composition is obtained by mixing at least one alkylaluminium halide with the product from the reaction caused by mixing at least one tungsten oxyhalide with at least one aryl isocyanate and/or diisocyanate.

12. A process according to claim 1, wherein the olefins are alpha olefins.

13. A process according to claim 1, characterised in that the olefins are selected from the group consisting of ethylene, propylene and but-1-ene.

14. A process according to claim 1, conducted between 0° C. and 100° C. and at a pressure which is sufficient to keep at least part of the reactants in the liquid phase.

15. A process according to claim 1, wherein the olefins have 2–10 carbon atoms.

* * * * *